US006455752B1

(12) United States Patent
Vesey

(10) Patent No.: US 6,455,752 B1
(45) Date of Patent: Sep. 24, 2002

(54) DECORATIVE ADHESIVE BANDAGE KIT

(76) Inventor: Kim Stella Vesey, 26-1D Bloomingdale Dr., Somerville, NJ (US) 08876

( * ) Notice: Subject to any disclaimer, the term of this patent is extended or adjusted under 35 U.S.C. 154(b) by 0 days.

(21) Appl. No.: 09/996,106

(22) Filed: Nov. 28, 2001

Related U.S. Application Data

(63) Continuation of application No. 09/563,571, filed on May 3, 2000, now abandoned, which is a continuation of application No. 09/165,563, filed on Oct. 2, 1998, now abandoned.

(51) Int. Cl.$^7$ ................................................. A61F 13/00
(52) U.S. Cl. ............................. 602/41; 602/54; 602/58; 206/440; 206/441; 206/575
(58) Field of Search .................... D24/189; 602/41–59; 128/888, 889; 206/440, 441

(56) References Cited

U.S. PATENT DOCUMENTS

| 3,645,835 A | | 2/1972 | Hodgson |
|---|---|---|---|
| 4,094,316 A | * | 6/1978 | Nathanson .................... 602/57 |
| 4,285,338 A | | 8/1981 | Lemelson |
| 4,499,896 A | | 2/1985 | Heinecke |
| 4,661,105 A | | 4/1987 | Gale |
| 4,927,025 A | | 5/1990 | Thompson |
| 5,275,284 A | | 1/1994 | Onotsky |
| 5,962,110 A | | 10/1999 | Penke-Wevelhoff |

FOREIGN PATENT DOCUMENTS

| GB | 2217206 A | 10/1989 |
|---|---|---|
| WO | WO 94/23677 A2 | 10/1994 |

OTHER PUBLICATIONS

Front and back image of a product packaging card, said product marketed by Lisa Frank, Inc.; believed to have been purchased in the U.S. in 1988 prior to the filing of the priority application of the present case.

Search report of International Application PCT/US99/22963, the international application corresponding to the parent application of the present case.

Derwent abstract of FR 2,425,240.

Derwent abstract of BE 1,009,757.

Front, back and side images of a box of Sticker Bandages marketed by Dayton Hudson Corp.; believed to have been purchased in the U.S. in 1999 after the filing of the priority application of the present case.

* cited by examiner

Primary Examiner—Kim M. Lewis
(74) Attorney, Agent, or Firm—Fredrick L. Herman

(57) ABSTRACT

The present invention is for a kit containing components for making decorated adhesive bandages. The kit comprises: a) at least one adhesive bandage comprising a backing, an adhesive layer on one side thereof and an absorbent pad affixed to the adhesive; and b) at least one decorative element selected from adhesive stickers and adhesive tattoos. The decorative element comprises a substrate, a decorative pattern thereon and an adhesive layer. The decorative element is designed to be securely fixed to the upper surface of the bandage. The decorative element is separate from and unsecured to the bandage in the kit. The decorative elements are preferably stickers. By carefully selecting and matching the materials in the bandages and the decorative elements, decorative bandages that are flexible, conformable, and contain a decoration that is resistant to delamination under wet and dry conditions may be custom-made by the consumer at point-of-use.

27 Claims, 3 Drawing Sheets

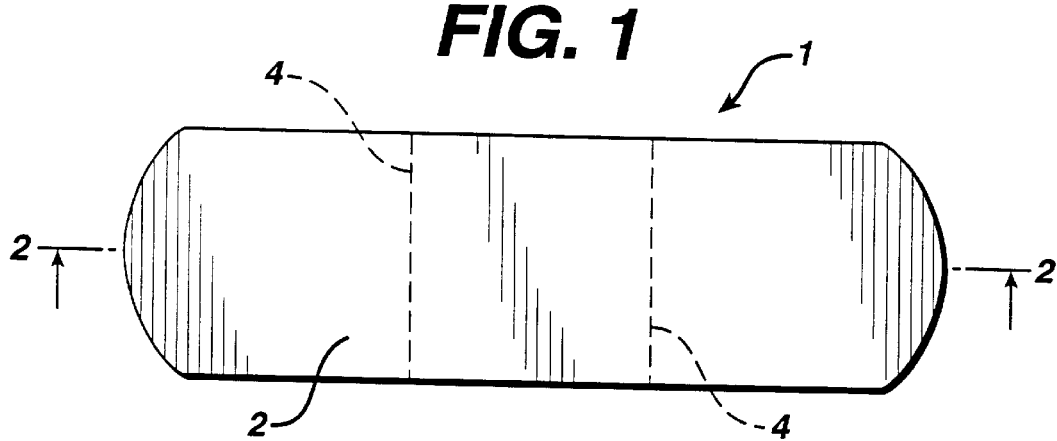
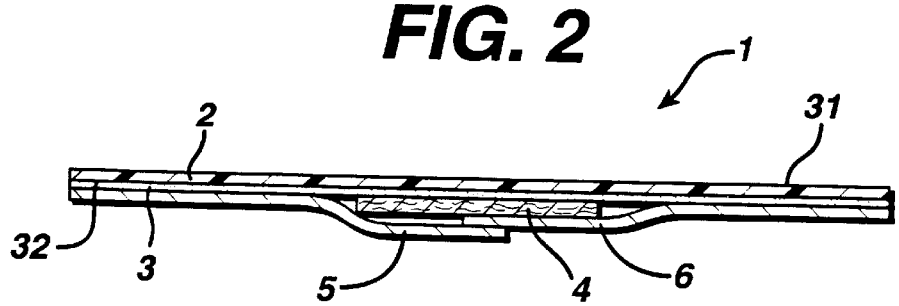
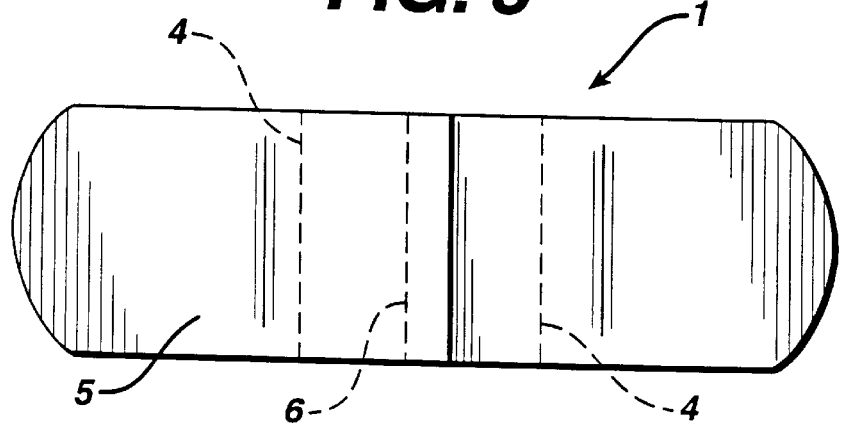

DECORATIVE ADHESIVE BANDAGE KIT

This application is a continuation of Ser. No. 09/563,571 filed May 3, 2000, abandoned, which is a continuation of Ser. No. 09/165,563 filed Oct. 2, 1998, abandoned.

FIELD OF THE INVENTION

The present invention relates to a kit for the formation of decorative adhesive bandages, particularly for the treatment of wounds on children.

BACKGROUND OF THE INVENTION

U.S. Pat. No. 4,094,316 discloses an adhesive bandage with a reusable applique in sheet form. The applique is pre-attached to the bandage, is preferably made of cloth and is of substantially the same size as the underlying bandage to which it is attached.

U.S Pat. No. 4,285,338 discloses an adhesive bandage with a rigid plastic shell attached to its outside surface. The shell serves to protect against force applied to the wound. The shell may be molded to a novelty configuration.

Lisa Frank Inc. of Tucson, Ariz. markets a product in which a reclosable plastic container is enclosed within a blister package. The reclosable container contains a plurality of decorated adhesive bandages, each individually wrapped in known fashion. The decoration on the pre-decorated bandages extends over substantially the entire surface area of the bandage backing. The bandage itself is about 72 mm long and about 19 mm wide. The decorative imprint is about 72 mm long and about 16 mm wide. The reclosable container also contains two sheets of decorative adhesive stickers. The directions and pictorial illustrations provided on the blister pack do not direct or suggest to the consumer that the decorative adhesive stickers are intended to be applied to the bandage. Furthermore, the stickers in the above-mentioned product are made of paper, do not adhere particularly well to the accompanying bandages, and if applied to the accompanying bandages, delaminate easily during normal wear of the bandage.

Accordingly, it is an object of the present invention to provide a kit, particularly for use by children, which enables children to custom-decorate their bandages.

It is another object of the invention to provide a decorative bandage kit that permits consumers to decorate their bandages at the point of use.

It is another object of the invention to provide decorations for use on bandages that once applied, remain securely fixed to the bandage.

It is another object of the invention to provide a bandage kit that contains flexible decorative elements that conform to the movement of the part of the body to which the bandage is secured.

It is another object of the invention to provide a bandage kit for making decorated bandages in which the decorative element remains attached to the bandage in wet environments.

It is another object of the invention to provide a bandage kit which provides a play element for the children for whom the bandages are intended.

It is another object of the invention to provide a kit which creatively involves children in the healing process.

These and other objects are obtained in the decorative bandage kit of the present invention.

BRIEF SUMMARY OF THE INVENTION

The present invention is for a kit containing components for making decorated adhesive bandages. The kit comprises:

a) at least one adhesive bandage comprising a backing, an adhesive layer on one side thereof and an absorbent pad affixed to the adhesive; and b) at least one decorative element selected from adhesive stickers and adhesive tattoos. The decorative element comprises a substrate, a decorative pattern thereon and an adhesive layer. The decorative element is designed to be securely fixed to the upper surface of the bandage. The decorative element is separate from and unsecured to the bandage in the kit.

c) instructions that suggest the use of said at least one decorative element to decorate said at least one adhesive bandage.

BRIEF DESCRIPTION OF THE DRAWINGS

FIG. 1 is a top plan view of one embodiment of an adhesive bandage which may be included in the kit of the present invention;

FIG. 2 is a cross-section taken along line 2—2 of FIG. 1;

FIG. 3 is a bottom plan view of the bandage shown in FIG. 1;

DETAILED DESCRIPTION OF THE INVENTION

Figure 4:
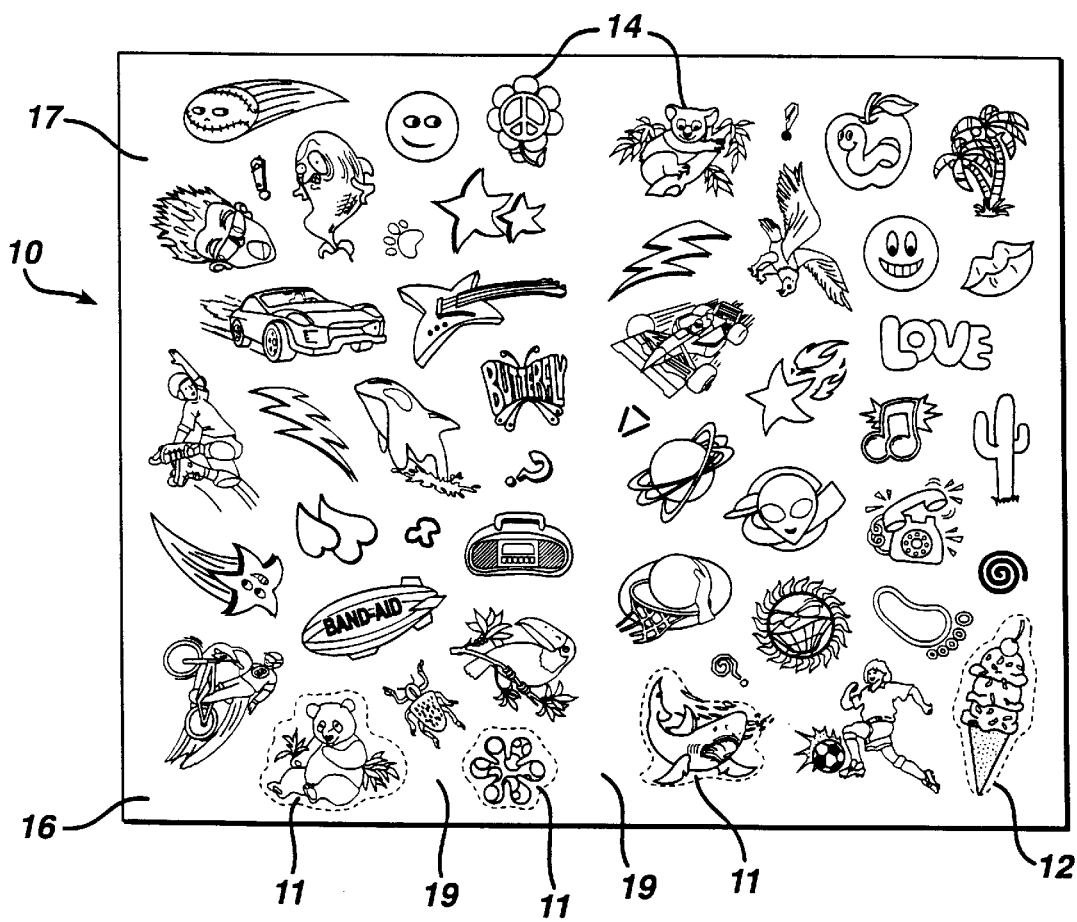
FIG. 4 is a sheet containing stickers used in one embodiment of the kit of the invention.

The kit of the invention comprises at least one and preferably a plurality of adhesive bandages. A bandage which may be used in the kit of the invention is shown in FIGS. 1–3 of the accompanying drawings. Bandage 1 comprises a backing strip 2, a layer of adhesive 3, an absorbent, wound contacting pad 4, and a pair of protective release tabs 5 and 6.

As illustrated, backing strip 2 is rectangular in configuration and comprises a first major, or upper, surface 31 and a second major, or lower, surface 32. Backing strip 2 may assume other configurations, e.g., the backing may be square or circular. Adhesive 3, which may be any of the well-known adhesive materials used for adhesive bandages, is applied to lower surface 32 of backing strip 2.

Absorbent pad 4 is secured to the lower surface of is bandage 1 by adhesive 3. The absorbent pad is typically a nonwoven material made from rayon fibers or polyester fibers or a blend of such fibers. It will be apparent to those skilled in the art that other fibers, e.g., cotton fibers or polyolefin fibers may be used in constructing the absorbent pad.

As seen in the drawings, absorbent pad 4 is centered from end-to-end of the bandage and its side edges ate co-extensive with the longitudinally extending edges of backing strip 2. The bandage may assume other configurations known in the art. For example, bandage 1 may have an "island construction", i.e., absorbent pad 4 may be located on backing strip 2 such that its end and side edges are spaced inwardly from the adjacent end and side edges of backing strip 2.

Bandage 1 also comprises a pair of adhesive protecting release tabs 5, 6 which may be made, e.g., from paper having a silicone release material coated thereon. Alternatively, the release tabs may be made of a low surface energy plastic film such as polyethylene or polystyrene which, if desired, may have a silicone release material or the like applied thereto. It will be understood that the release coated surface of tabs 5, 6 will contact adhesive 3 and the release coating on release tabs 5, 6 will be such that adhesive 3 will remain on bandage backing 2 rather than on the release tabs when those tabs are removed to expose the adhesive prior to application of the bandage to the skin.

The bandages used in the kits of the invention are preferably individually packaged between two sheets of a material such as paper which are sealed cohesively about their edges.

The kit of the invention may contain a plurality of bandages all of which may be of the same size. Alternatively, the kit may comprise bandages of different sizes for treating different sized wounds.

The backing of the bandage may be selected from a plastic film, a plastic foam, a woven fabric, a nonwoven fabric or a knitted fabric. Alternatively, the backing may be a composite comprising two or more of these elements, such as a composite of a film and a nonwoven fabric. A plastic film backing is preferred for use in the bandages contained in the kit of the invention. If made from a film or foam, the bandage backing is preferably perforated.

The materials that may be useful in making the backing of the bandage include polyethylene, polyurethane, polyvinyl chloride and plasticized polyvinyl chloride. Polyvinyl chloride and plasticized polyvinyl chloride are preferred, and plasticized polyvinyl-chloride is most preferred.

The adhesive layer comprising the bandages in the kits of the invention may be of any skin-compatible adhesive material known in the bandage art. Exemplary adhesive materials include acrylic emulsion adhesive, solvent-based acrylic adhesive, acrylic hot melt adhesive, styrene-olefin copolymer such as styrene-isoprene-styrene block copolymer, natural rubber and silicone adhesive. Of these, an acrylic pressure-sensitive adhesive is preferred, and specifically, an acrylic emulsion pressure sensitive adhesive is most preferred.

The kit of the invention further comprises at least one and preferably a plurality of decorative elements 11. The decorative elements may be selected from adhesive stickers and adhesive tattoos. Of these, adhesive stickers are preferred.

Figure 5:
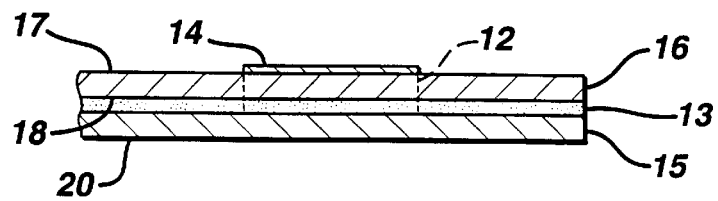
FIG. 5 is a partial cross-section of the sheet of FIG. 4.
Figure 6:
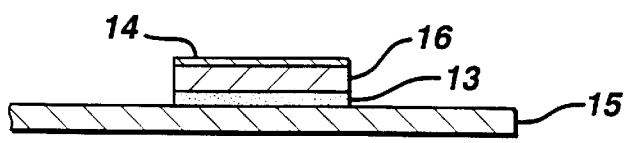
FIG. 6 is a partial cross-section of an alternate embodiment of a sheet containing stickers for use in the kits of the invention.

Stickers for use in the kits of the invention are shown in FIGS. 4, 5 and 6. Adhesive stickers are typically supplied on a sheet of release paper 15. The sticker comprises a substrate 16. Decorative pattern 14 is typically printed on the upper surface 17 of substrate 16. The surface of the substrate opposite the printed pattern, i.e., lower surface 18, carries adhesive layer 13. The surface of release paper 15 to which the stickers are attached includes a coating which allows the stickers to be removed from the sheet while the adhesive adheres to the sticker.

A plurality of stickers on a sheet of release paper is shown in FIG. 4. As shown in FIG. 4, sheet 10 contains a plurality of stickers 11. The decorative elements 11 are typically made by printing a decorative pattern 14 onto surface 17 of substrate 16. Each sticker is circumscribed by score lines 12 to permit lifting individual stickers from release sheet 15. The sticker is removed from the release paper sheet by bending the sheet adjacent one of the score lines 12. This causes an edge of the sticker to lift off the release sheet and to be separated from adjacent portions 19 of substrate 16 which are intermediate adjacent stickers 11. Once an edge of the sticker is exposed and removed from the release sheet, the sticker may be grasped with the fingers, lifted off the sheet in its entirety and applied to upper surface 31 of bandage 1 supplied in the kit of the invention.

In an alternate embodiment shown in cross-section in FIG. 6, sheets containing stickers are supplied in which portions of substrate 19 intermediate adjacent stickers are removed from release paper 15.

As shown in FIG. 4, a sheet of decorative elements may contain a virtually limitless number of decorative patterns and motifs. Exemplary motifs include sports motifs, animals, celestial bodies, geometrical shapes, letters, words, flowers, cartoon characters, cars, birds, insects and the like.

The decorated bandages produced from the kits of the invention should have the following desirable characteristics: First, they should be durable. This means that the decorative element, once applied, should remain securely fixed to the surface of the bandage. Preferably, the decorative element should remain firmly affixed to the bandage in wet as well as under dry conditions. The decorative element should be not be easily abraded from the bandage and it should be tear-resistant. Second, the decorated bandage, as well as its individual elements, should be flexible and conformable, so that the decorative elements do not delaminate when, for example, the bandage is placed on a joint and the joint is flexed repeatedly. These properties are achieved by careful design and selection of materials that comprise the decorative element and by carefully matching the decorative elements with their accompanying bandages in the kits of the invention.

The substrate 16 of the decorative element may be selected from plastic film comprising a polymer selected from polyethylene, polypropylene, polyester, polyvinyl chloride and plasticized polyvinyl chloride; a metallized plastic film; and a metal foil. Preferably, the substrate is a plastic film comprising a polymer selected from polyvinyl chloride and plasticized polyvinyl chloride. Most preferably, the substrate is a plastic film comprising plasticized polyvinyl chloride.

The material comprising the decorative element substrate should preferably be the same material that comprises the bandage backing in order that the decorative element and the bandage will have substantially the same flexibility characteristics in use. Preferably, both the decorative element substrate and the bandage backing comprise plasticized polyvinyl chloride.

In addition to materials selection, the decorative element substrate thickness should also be carefully selected to optimize the properties of the decorative bandage. The substrate thickness should be in the range of about 0.0005 inches to about 0.006 inches. Preferably, the thickness of substrate 16 should be about 0.002 to about 0.004 inches. At smaller thickness, the decorative element becomes difficult to handle as it is removed from its release sheet. At larger thickness, the decorative element loses flexibility and conformability.

The choice of adhesive material for the decorative element depends on the materials comprising the bandage backing and the decorative element substrate. The adhesive is a pressure sensitive adhesive, preferably selected from an acrylic emulsion, a solvent-based acrylic, an acrylic hot melt, a styrene-olefin copolymer such as styrene-isoprene-styrene block copolymer, natural rubber and silicone adhesive. When the bandage backing and decorative element substrate comprise plasticized polyvinyl chloride, the adhesive is preferably an acrylic pressure sensitive adhesive, and most preferably, an acrylic emulsion pressure sensitive adhesive.

The adhesive layer is contained in the decorative element at a dry weight of between about 10 about 100 grams per square meter of decorative element surface area. Preferably the adhesive is contained in the decorative element at a dry weight of about 20 to about 50 g/m² of surface area.

The decorative elements are preferably sized to fit in their entirety on at least one of the adhesive bandages contained in the kit without extending beyond the edges of said bandage.

The bandages used in the kits of the invention are preferably substantially undecorated, i.e., the bandage backing is free of the decorative patterns of the type contained on the decorative elements. The bandage backing may be clear or it may be translucent or opaque. Alternatively, the bandage backing may be printed with a regular pattern such as a cross-hatch pattern. Preferably, the bandage backing is clear. Use of decorative elements on a clear bandage is desirable because it provides the illusion of a tattoo on the skin surface.

The substrate material comprising the decorative element is preferably opaque because opaque substrates are better at "bringing out," or highlighting the colors of the decorative pattern contained thereon.

The kits of the invention preferably contain a plurality of decorative elements and a plurality of bandages in a reclosable container. Exemplary materials that comprise the container include paper, cardboard, metal and plastic.

The kits of the invention preferably contain indicia that indicate that the decorative elements are intended for use and may be used in conjunction with the accompanying bandages to decorate said bandages. These indicia may be in the form of graphics or text or a combination of these. The indicia may be displayed on the exterior of the container, on the reverse side 20 of the decorative element release sheet 15 or on a separately enclosed insert in the kit container or on a combination of these locations.

Figure 7:
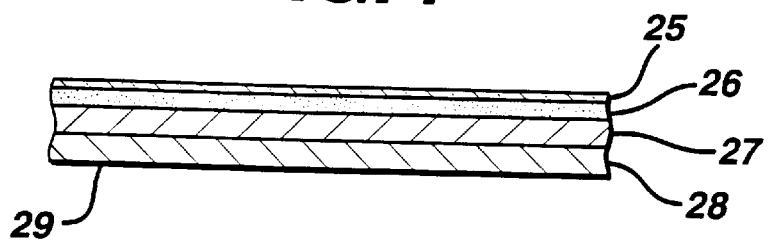
FIG. 7 is a partial cross-section view of a sheet of tattoos for use in the kits of the invention.

As indicated previously, an alternate embodiment for the decorative element is a "tattoo." A tattoo is depicted in cross-section in FIG. 7. As shown in FIG. 7, the tattoo consists of a clear plastic film 25 which is removable from the tattoo. Adjacent the film 25 is an adhesive layer 26. Adjacent the adhesive on the side opposite the clear plastic film is substrate layer 27 on which a decorative pattern is printed. The substrate 27 is supported on carrier paper 28. In use, the tattoo is applied to the substantially undecorated bandage by removing clear plastic film 25, and adhering the remainder thereof to the bandage with adhesive film 26. The underside 29 of carrier paper 28 is then moistened, and, after waiting a brief time, carrier paper 28 is removed from the tattoo.

EXAMPLE

A sheet of decorative stickers is prepared from white pigmented opaque plasticized polyvinyl chloride film (JK4709W film from the Occidental Chemical Corp. of Burlington, N.J.) having a thickness of about 0.003 inches. An acrylic emulsion polymer is applied to the release surface of a silicone-coated release sheet. The acrylic emulsion comprises a polymer primarily (>80%) of 2-ethylhexyl acrylate with minor amounts (less than 20%) of vinyl acetate and other monomers. The emulsion contains about 50% solids. Suitable emulsion polymers are well known in the art and are widely available commercially. One such polymer useful in this regard is acrylic emulsion pressure sensitive adhesive AE1200 available from the Chemical Division of Avery Dennison of Mill Hall, Pa. The emulsion is applied to the release paper at a coating weight of 35 g/m² on a dry solids basis. The volatiles are evaporated from the emulsion in an oven and the plasticized polyvinyl chloride film is laminated to the adhesive on the release paper to form a release paper-adhesive-film laminate. Decorative multicolor patterns shown in FIG. 4 are printed on the film surface of the laminate using UV curing inks. A top-coat of a clear varnish is applied after printing the decorative pattern to further increase the durability of the pattern. Following UV curing, the sheet containing the decorative patterns is kiss-scored using a scoring knife that contains blades in registration with the pattern printed on the laminate. The blade height is set to cut through the substrate thickness without cutting through the release paper.

Adhesion of the decorative element to a bandage was determined as follows:

The stickers produced as described above were applied to clear BAND-AID® brand adhesive bandages marketed by Johnson & Johnson Consumer Products Company, a division of Johnson & Johnson Consumer Companies, Inc. The backing of these bandages comprises plasticized polyvinyl chloride film. The bandages were applied to the finger joints on one hand. As a comparative example, the stickers and bandages marketed by Lisa Frank, Inc. referred to above were applied to the finger joints of the other hand. The fingers on both hands were flexed corresponding to normal daily activity. Soon after initiation of the test, the stickers supplied by Lisa Frank, Inc. began to delaminate from the bandages at their outer edges, which indicated early expected failure of these components. In contrast, the stickers useful in the kits of the invention described in the above example remained in place with no sign of delamination from their underlying bandages.

Adhesion of the decorative elements to a bandage under wet conditions was assessed as follows:

Five tests were performed. In each of these, bandages were decorated by applying a sticker to the upper surface of a Johnson & Johnson Clear BAND-AID® brand adhesive bandage above the pad area of the bandage. Sixteen panelists applied the test bandages to their fingers. After applying the bandages, the panelists soaked their hands in 100° F. soapy water for 10 minutes while flexing their fingers. The degree of adhesion of the stickers to the bandages after being subjected to the above-described soaking conditions was assessed using the following scale:

1=approximately 1–15% of the sticker is adhered
2=approximately 16–30% of the sticker is adhered
3=approximately 31–45% of the sticker is adhered
4=approximately 46–60% of the sticker is adhered
5=approximately 61–75% of the sticker is adhered
6=approximately 76–90% of the sticker is adhered
7=sticker is completely adhered The stickers used in these tests are shown in Table 1 and the adhesion test results are shown in Table 2.

TABLE 1

Stickers Used in Wet Adhesion Tests

| | Test 1 | Test 2 | Test 3 | Test 4 | Test 5 |
|---|---|---|---|---|---|
| Sticker | Sticker of the Invention per the above Example | Sticker of the Invention per the above Example | Sticker of the Invention per the above Example | SANDYLION Paper Stickers No. PKK332* | Lisa Frank, Inc.** Paper Stickers No. P-468 |

*Sandylion Sticker Designs of Markham, Ontario Canada
**Lisa Frank, Inc. of Tucson, AZ

TABLE 2

Wet Adhesion of Stickers to Bandages

| Subject No. | Test 1 | Test 2 | Test 3 | Test 4 | Test 5 |
|---|---|---|---|---|---|
| 1 | 6 | 7 | 7 | 0 | 0 |
| 2 | 7 | 7 | 7 | 0 | 0 |
| 3 | 7 | 6 | 7 | 0 | 0 |
| 4 | 6 | 7 | 7 | 0 | 5 |
| 5 | 7 | 7 | 7 | 0 | 2 |
| 6 | 7 | 7 | 6 | 0 | 0 |
| 7 | 7 | 7 | 7 | 0 | 0 |
| 8 | 7 | 7 | 7 | 0 | 1 |
| 9 | 7 | 7 | 7 | 0 | 1 |
| 10 | 7 | 7 | 7 | 0 | 5 |
| 11 | 7 | 7 | 7 | 0 | 6 |
| 12 | 7 | 6 | 7 | 0 | 0 |
| 13 | 7 | 6 | 7 | 0 | 3 |
| 14 | 7 | 7 | 7 | 0 | 1 |
| 15 | 7 | 7 | 7 | 0 | 2 |
| 16 | 7 | 7 | 7 | 0 | 2 |
| Average Score | 6.88 | 6.81 | 6.94 | 0.00 | 1.75 |
| No. of Failures | 0 | 0 | 0 | 16 | 6 |

The data in the tables indicate that excellent adhesion is obtained under wet conditions using the decorative stickers used in the above-described example. In contrast, wet adhesion to the bandages is very poor using prior art stickers.

Figure 8:
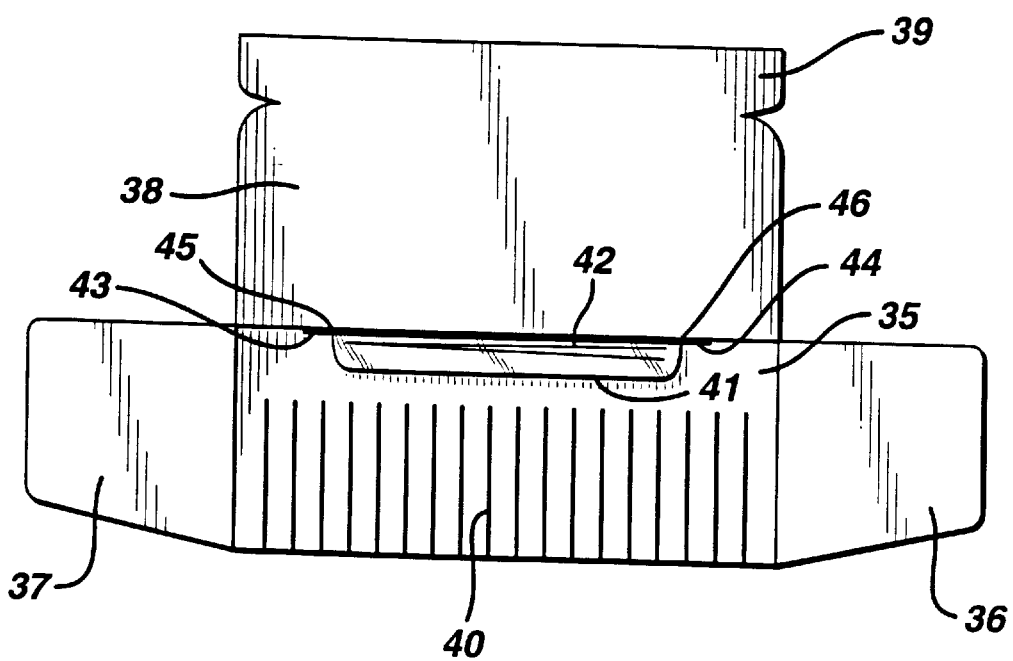
FIG. 8 is a top plan view of an open carton comprising the kit of the invention.

FIG. 8 shows a top plan view of a kit of the invention in a reclosable carton. The carton 35 has side flaps 36 and 37 and top flap 38 with insert portion 39 that tucks into the carton when the carton is closed. The kit comprises individually wrapped adhesive bandages 40. The kit further comprises plastic pouch 41 adhered to one inner surface of the carton at edges 43 and 44. The pouch contains a folded over sheet of stickers 42 on a sheet of release paper. The pouch contains score lines running along the height of the pouch at 45 and 46 in FIG. 8. The pouch score lines permit the pouch to be easily removed from the carton. The carton is decorated on its outside with text and graphics indicia which indicate that the carton contains both bandages and decorative stickers and that the stickers are to be used in decorating the bandages.

What is claimed is:

1. A kit comprising components for making a decorated adhesive bandage, said kit comprising:
   a) at least one adhesive bandage comprising a backing, an adhesive layer on one side thereof and an absorbent pad affixed to said adhesive;
   b) at least one decorative element selected from adhesive stickers and adhesive tattoos; said decorative element comprising a substrate, a decorative pattern thereon and an adhesive layer, said decorative element being designed to be securely fixed directly to the upper surface of said bandage, said decorative element being separate from said bandage in said kit; and
   c) instructions that suggest the use of said at least one decorative element to decorate said at least one adhesive bandage.

2. The kit of claim 1 which comprises a plurality of adhesive bandages.

3. The kit of claim 2 which comprises adhesive bandages of at least two different sizes.

4. The kit of claim 1 wherein the bandage backing comprising a plastic film, said plastic film comprising a polymer selected from polyethylene, polyurethane, polyvinyl chloride and plasticized polyvinyl chloride.

5. The kit of claim 4 wherein the bandage backing plastic film comprises a polymer selected from polyvinyl chloride and plasticized polyvinyl chloride.

6. The kit of claim 1 wherein said bandage further comprises release tabs and each bandage in said kit is individually wrapped.

7. The kit of claim 1 wherein said decorative element is an adhesive sticker.

8. The kit of claim 1 which comprises a plurality of decorative elements.

9. The kit of claim 8 wherein a plurality of decorative elements are adhered to a sheet of release paper.

10. The kit of claim 1 wherein said decorative element substrate is selected from a plastic film comprising a polymer selected from polyethylene, polypropylene, polyester, polyvinyl chloride and plasticized polyvinyl chloride; a metalized plastic film; and a metal foil.

11. The kit of claim 10 wherein said decorative element substrate is a plastic film comprising a polymer selected from polyvinyl chloride and plasticized polyvinyl chloride.

12. The kit of claim 10 wherein said decorative element substrate plastic film has a thickness of about 0.0005 inches to about 0.006 inches.

13. The kit of claim 10 wherein said decorative element substrate plastic film has a thickness of about 0.002 inches to about 0.004 inches.

14. The kit of claim 1 wherein said decorative element adhesive layer comprises an adhesive selected from an acrylic emulsion, a solvent-based acrylic, an acrylic hot melt, a styrene-olefin copolymer, natural rubber and silicone adhesive.

15. The kit of claim 14 wherein said decorative element adhesive layer comprises an adhesive selected from an acrylic emulsion, a solvent-based acrylic and an acrylic hot melt adhesive.

16. The kit of claim 1 wherein said decorative element is sized to fit in its entirety on the adhesive bandage without extending beyond the edges of said bandage.

17. The kit of claim 1 wherein said bandage backing comprises a plasticized polyvinyl chloride film and said decorative element substrate comprises a plasticized polyvinyl chloride film.

18. The kit of claim 17 wherein said decorative element adhesive layer comprises an acrylic pressure sensitive adhesive.

19. The kit of claim 1 wherein said bandage backing is substantially undecorated.

20. The kit of claim 19 wherein the bandage backing is optically clear.

21. The kit of claim 1 comprising a plurality of bandages and decorative elements and wherein said bandages and decorative elements are packaged in a reclosable container.

22. The kit of claim 1 wherein the decorative element substrate is opaque.

23. The decorated bandage produced using the adhesive bandage and decorative element of claim 1.

24. The decorated bandage of claim 23 wherein the decorative element is resistant to delamination from the bandage under wet conditions.

25. The kit of claim 1 wherein the instructions are in the form of graphical indicia, textual indicia, or a combination of graphical and textual indicia.

26. The kit of claim 1 wherein said kit is packaged in a container and said instructions are contained on the exterior of said container.

27. The kit of claim 1 wherein said kit is packaged in a container and said instructions are contained in the interior of said container.

\* \* \* \* \*